United States Patent
Al et al.

(10) Patent No.: US 11,760,972 B2
(45) Date of Patent: Sep. 19, 2023

(54) ENHANCED EFFICIENT NITROGEN-FIXING COMPOSITE MICROBIAL SYSTEM ADDED WITH NON-NITROGEN-FIXING BACTERIA AND APPLICATION THEREOF

(71) Applicant: Institute of Agricultural Resources and Regional Planning, CAAS, Beijing (CN)

(72) Inventors: Chao Al, Beijing (CN); Liyu Zhang, Beijing (CN); Wei Zhou, Beijing (CN)

(73) Assignee: INSTITUTE OF AGRICULTURAL RESOURCES AND REGIONAL PLANNING, CAAS, Beijing (CN)

( * ) Notice: Subject to any disclaimer, the term of this patent is extended or adjusted under 35 U.S.C. 154(b) by 0 days.

(21) Appl. No.: 18/073,169

(22) Filed: Dec. 1, 2022

(65) Prior Publication Data

US 2023/0101720 A1   Mar. 30, 2023

Related U.S. Application Data

(63) Continuation of application No. PCT/CN2022/092763, filed on May 13, 2022.

(30) Foreign Application Priority Data

May 21, 2021 (CN) .......................... 2021105606520

(51) Int. Cl.
  *C05F 11/08* (2006.01)
  *A01N 63/20* (2020.01)
  *C12N 1/20* (2006.01)

(52) U.S. Cl.
  CPC ............ *C12N 1/205* (2021.05); *A01N 63/20* (2020.01); *C05F 11/08* (2013.01)

(58) Field of Classification Search
  None
  See application file for complete search history.

(56) References Cited

FOREIGN PATENT DOCUMENTS

AU       2021103149 A4 *  8/2021

* cited by examiner

*Primary Examiner* — Alton N Pryor
(74) *Attorney, Agent, or Firm* — WPAT, PC

(57) ABSTRACT

Disclosed are an enhanced efficient nitrogen-fixing composite microbial system added with non-nitrogen-fixing bacteria and application thereof, belonging to the technical field of agricultural microorganisms. The present disclosure provides enhanced efficient nitrogen-fixing bacteria, including at least one selected from a group of *Klebsiella* MNAZ1050, *Citrobacter* MNAZ1397 and *Pseudomonas* MNAZ228; also, the disclosed enhanced efficient nitrogen-fixing composite microbial system includes nitrogen-fixing bacteria and non-nitrogen-fixing bacteria, where the nitrogen-fixing bacteria includes at least one of the above three nitrogen-fixing bacteria, and the non-nitrogen-fixing bacteria includes at least one of *Acinetobacter* ACZLY512 and *Kluyvera* AZ981.

4 Claims, 5 Drawing Sheets

ENHANCED EFFICIENT NITROGEN-FIXING COMPOSITE MICROBIAL SYSTEM ADDED WITH NON-NITROGEN-FIXING BACTERIA AND APPLICATION THEREOF

CROSS-REFERENCE TO RELATED APPLICATIONS

This application claims priority to Chinese Patent Application No. 202110560652.0, filed on May 21, 2021, the contents of which are hereby incorporated by reference.

TECHNICAL FIELD

The present disclosure relates to the technical field of agricultural microorganisms, and specifically relates to an enhanced efficient nitrogen-fixing composite microbial system added with non-nitrogen-fixing bacteria and application thereof.

BACKGROUND

Nitrogen fertilizer is crucial for high and stable crop yields and contributes to more than 50 percent (%) of crop yield increase. However, a series of ecological and environmental problems, such as soil acidification, greenhouse gas emission, eutrophication of water bodies, and excessive nitrate content of agricultural products, have been resulted when large-scale application of nitrogen fertilizers began globally, especially in some countries and regions that have overused nitrogen fertilizers, which seriously impede the sustainable development of global agriculture; in this context, biological nitrogen fixation becomes one of the important ways to reduce the application of nitrogen fertilizer in agriculture. Presently, the nitrogen-fixing microorganisms identified are all bacteria, which, judging from the classification of plant endophytic nitrogen-fixing bacteria with full genomes, are mainly distributed in the orders Rhizobiales and Rhodospirillales of alpha proteobacteria (α-proteobacteria), Burkholderiales of beta-proteobacteria (β-proteobacteria), Enterobacteriales of gamma-proteobacteria (γ-proteobacteria) and Bacillales of Firmicutes. Endophytic nitrogen-fixing bacteria colonize inside the plant and form an efficient nitrogen fixation system in ecological niches with sufficient nutrients and suitable microenvironment, providing nitrogen nutrients to the host crop while promoting growth of the host crop with secreted phytohormones in addition to other means.

Researches on endophytic nitrogen-fixing bacteria in plants across the world mainly focus on the screening and application of single strain of nitrogen-fixing bacteria, examples of which include Rice endotrophic azotobacter for improving disease resistance and stress resistance of crops and purpose thereof (CN102286400A), Sugarcane endogenous burkholderia sp. CZ08152 and application thereof (CN108148785A), Endophytic azotobacter of wheat producing ACC (1-aminocyclopropane-1-carboxylate) deaminase and application thereof (CN102250808A), etc.; yet, none of the above inventions considered the synergistic effects between nitrogen-fixing bacteria and between nitrogen-fixing bacteria and non-nitrogen-fixing bacteria.

As mentioned above, the nitrogen-fixing bacteria mentioned in different inventions have different nitrogen-fixing ability or other functions, and exhibit different functions for different species of plants or a varying performance of the same function for the same plant, so it is important to develop new strains of nitrogen-fixing bacteria with better nitrogen-fixing ability or new functions for crop production. However, microorganisms in natural ecosystems exist independently rather than as a single strain, but form a complex biological network with other microorganisms and habitats to maintain the normal function of the ecosystem through interactions and functional complementation. Therefore, an efficient nitrogen-fixing composite microbial system is expected by artificial simulation and system reconstruction through the isolation and culture of nitrogen-fixing bacteria and bioinformatics analysis, which is based on the microbiology perspective of targeting the function of nitrogen-fixing microorganisms and extent the traditional concept of single microorganism, single environmental element and single microscopic process, and the developed efficient nitrogen-fixing composite microbial system, compared with single strains, provides better results in practical applications. For this reason, it is of practical significance to develop more functional high-efficiency nitrogen-fixing composite microbial systems for different needs to solve the technical problems of the prior art.

SUMMARY

The present disclosure provides an enhanced efficient nitrogen-fixing composite microbial system added with non-nitrogen-fixing bacteria and application thereof, where the composite microbial system includes nitrogen-fixing bacteria providing good nitrogen-fixing effect when being used alone, and providing even significant nitrogen-fixing performance after being used to construct a composite microbial system with non-nitrogen-fixing bacteria, promoting crop growth under obvious reduced amount of nitrogen fertilizer application.

To achieve the above objectives, the present disclosure provides the following schemes:

enhanced efficient nitrogen-fixing bacteria, including at least one selected from a group of *Klebsiella* MNAZ1050 (*Klebsiella* sp.), *Citrobacter* MNAZ1397 (*Citrobacter* sp.), and *Pseudomonas* MNAZ228 (*Pseudomonas* sp.);

the *Klebsiella* MNAZ1050, *Citrobacter* MNAZ1397, and the *Pseudomonas* MNAZ228 are all preserved in China General Microbiological Culture Collection Center (CGMCC) under a same preservation date of May 6, 2021, with a preservation number of *Klebsiella* MNAZ1050 being CGMCC No. 22270, and that of *Citrobacter* MNAZ1397 and *Pseudomonas* MNAZ228 being CGMCC No. 22267 and CGMCC No. 22266, respectively; the address of the CGMCC is No. 3, Courtyard No. 1, Beichen West Road, Chaoyang District, Beijing, China.

The present disclosure also provides an enhanced efficient nitrogen-fixing composite microbial system, including nitrogen-fixing bacteria and non-nitrogen-fixing bacteria, where the nitrogen-fixing bacteria include at least one selected form a group of *Klebsiella* MNAZ1050 (*Klebsiella* sp.), *Citrobacter* MNAZ1397 (*Citrobacter* sp.), and *Pseudomonas* MNAZ228 (*Pseudomonas* sp.), while the non-nitrogen-fixing bacteria include at least one selected form a group of *Acinetobacter* ACZLY512 (*Acinetobacter* sp.), *Kluyvera* AZ981 (*Kluyvera* sp.); the *Klebsiella* MNAZ1050, *Citrobacter* MNAZ1397, and the *Pseudomonas* MNAZ228 are all preserved in CGMCC under the same preservation date of May 6, 2021, with the preservation number of *Klebsiella* MNAZ1050 being CGMCC No. 22270, and that of *Citrobacter* MNAZ1397 and *Pseudomonas* MNAZ228 being CGMCC No. 22267 and CGMCC No. 22266, respectively; and the *Acinetobacter* ACZLY512 and the *Kluyvera* AZ981 are also preserved in CGMCC under the preservation date of May 6, 2021, with preservation number of *Acinetobacter* ACZLY512 being CGMCC No. 22268 and that of *Kluyvera* AZ981 being CGMCC No. 22269; the address of the CGMCC is No. 3, Courtyard No. 1, Beichen West Road, Chaoyang District, Beijing, China.

The present disclosure also provides a microbial inoculum, where the microbial inoculum includes the nitrogen-fixing composite microbial system as active ingredients.

Optionally, when the microbial inoculum includes two or more strains, the microbial inoculum is constructed according to any of the following proportions:

*Klebsiella* MNAZ1050 and *Citrobacter* MNAZ1397 in a ratio of (1-7):(1-4);

*Klebsiella* MNAZ1050 and *Pseudomonas* MNAZ228 in a ratio of (1-7):(1-2);

*Citrobacter* MNAZ1397 and *Pseudomonas* MNAZ228 in a ratio of (1-4):(1-2); and

*Klebsiella* MNAZ1050, *Citrobacter* MNAZ1397, and *Pseudomonas* MNAZ228 in a ratio of (1-7):(1-4):(1-2).

The present disclosure also provides a microbial inoculum, where the microbial inoculum includes the composite microbial system as active ingredients, and the nitrogen-fixing bacteria are in a ratio of (1-2):(1-2) to the non-nitrogen-fixing bacteria in the composite microbial system.

Optionally, when the microbial inoculum includes two or more nitrogen-fixing bacteria, the nitrogen-fixing bacteria include any of the following proportions:

*Klebsiella* MNAZ1050 and *Citrobacter* MNAZ1397 in a ratio of (1-7):(1-4);

*Klebsiella* MNAZ1050 and *Pseudomonas* MNAZ228 in a ratio of (1-7):(1-2);

*Citrobacter* MNAZ1397 and *Pseudomonas* MNAZ228 in a ratio of (1-4):(1-2); and

*Klebsiella* MNAZ1050, *Citrobacter* MNAZ1397, and *Pseudomonas* MNAZ228 in a ratio of (1-7):(1-4):(1-2).

The present disclosure also provides an application of the enhanced efficient nitrogen-fixing bacteria or the enhanced efficient nitrogen-fixing composite microbial system in preparing any of the following microbial inoculums:

(1) microbial inoculum for improving nitrogen fixation of food crops and agronomic crops;

(2) microbial inoculum for increasing aboveground biomass of food crops and agronomic crops; and (3) microbial inoculum for increasing root biomass of food crops and agronomic crops.

The present disclosure also provides a method for applying the enhanced efficient nitrogen-fixing bacteria or the enhanced efficient nitrogen-fixing composite microbial system or the microbial inoculum, where the enhanced efficient nitrogen-fixing bacteria or the enhanced efficient nitrogen-fixing composite microbial system or the microbial inoculum is used to treat roots of food crops or agronomic crops by means of root irrigation.

The present disclosure achieves the following technical effects:

by combining modern bioinformatics analysis with the isolation and cultivation of nitrogen-fixing bacteria, the present invention simplifies and reorganizes the composition of biological nitrogen-fixing bacteria community in maize and constructs an enhanced efficient nitrogen-fixing composite microbial system, which maintains efficient nitrogen-fixing activity under aerobic or microaerobic conditions; all strains in the enhanced efficient nitrogen-fixing composite microbial system are selected from five maize varieties, so there is no mutual exclusion between them and maize; consequently, the enhanced efficient nitrogen-fixing composite microbial system proposed in the present disclosure has excellent environmental adaptability;

moreover, the enhanced efficient nitrogen-fixing composite microbial system proposed by the present disclosure has a good promoting effect on maize growth with reduced nitrogen fertilizer application, with significant improvement of maize root growth, indicating that the enhanced efficient nitrogen-fixing composite microbial system can not only biologically fix nitrogen and provide nitrogen nutrition for maize, but also have root promotion effect, suggesting a good application prospect in food crop and horticultural crop production and other fields of the enhanced efficient nitrogen-fixing composite microbial system.

BRIEF DESCRIPTION OF THE DRAWINGS

In order to more clearly explain the embodiments of the present invention or the technical schemes in the prior art, the following will briefly introduce the drawings that need to be used in the embodiments. Obviously, the drawings in the following description are only some embodiments of the present disclosure. For those of ordinary skill in the art, other drawings can be obtained according to these drawings without any creative labor.

DETAILED DESCRIPTION OF THE EMBODIMENTS

Figure 1A:
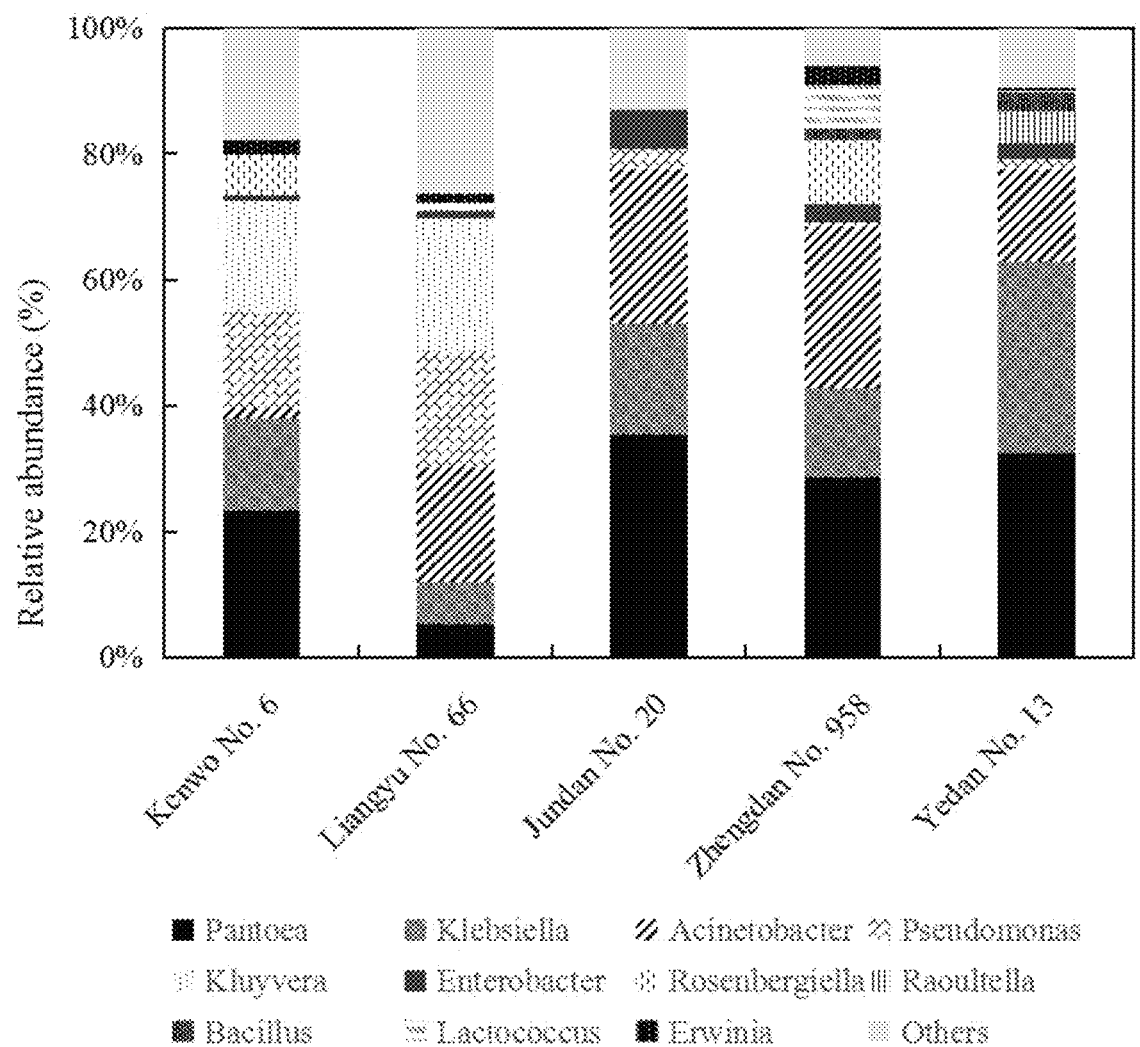
FIG. 1A-FIG. 1B show taxonomic information and network analysis results of 969 strains of bacteria obtained from five maize varieties at genus level.

The technical schemes of the present disclosure are now specified by way of embodiments, which should not be considered as a limitation of the present disclosure, but should be understood as a rather detailed description of certain aspects, features and embodiments of the present disclosure.

Experimental methods used in the following embodiments are conventional methods if no special instructions are given; materials and reagents used, unless otherwise specified, are reagents and materials available from commercial sources.

Embodiment 1 Construction of Enhanced Efficient Nitrogen-Fixing Composite Microbial System and Verification of Nitrogen Fixation Effect 1. Screening of Strains for the Composite Microbial Strains 1) saps are collected from conducting tissues of stems of five maize varieties, namely Kenwo No. 6, Liangyu No. 66, Jundan No. 20, Zhengdan No. 958 and Yedan No. 13, at an experimental base of the Institute of Agricultural Resources and Regional Planning (IARRP) of the Chinese Academy of Agricultural Sciences (CAAS), including: cutting off the stem of maize at a central position of a third node stem above a base of the maize, letting the sap of the conducting tissue flow out of a cross section of the stem under a root pressure of the maize, using a 0.5 gram (g) sterile absorbent cotton ball to absorb the sap, and storing the sterile absorbent cotton ball in a 50 milliliters (mL) sterile centrifuge tube, then placing the centrifuge tube on an ice surface and bringing it back to laboratory; and 2) 2 mL of 0.9 percent (%) sterile normal saline is added into the centrifuge tube with absorbent cotton ball in an ultra-clean workbench, followed by culture for 1 hour (h) in a shaking table at a speed of 160 revolutions per minute (rpm) and 28 degree Celsius (° C.) to obtain a fully mixed liquid; then the mixed liquid is diluted 10 times to obtain a diluted liquid, and 100 microliters (μL) of the diluted liquid is coated onto a R2A solid medium, followed by culture at 28° C. for 2-4 days; then strains as colonies emerge on the solid medium are picked out and purified 3 times by streaking method, and the strains after purification are stored in 30% glycerol at −70° C.;

the R2A solid medium (gL$^{-1}$) includes the following components: yeast extract 0.5 g, peptone 0.5 g, casein hydrolysate 0.5 g, glucose 0.5 g, starch 0.5 g, sodium pyruvate 0.3 g, dipotassium hydrogen phosphate 0.3 g, magnesium sulfate 0.05 g and agar 15.0 g; and 3) the strains are subjected to 16S rDNA sequence analysis, with results showing a total of 1,574 pure bacteria are collected from the saps of conducting tissues of the five maize varieties, and 969 strains have different 16S rDNA.

Figure 1B:
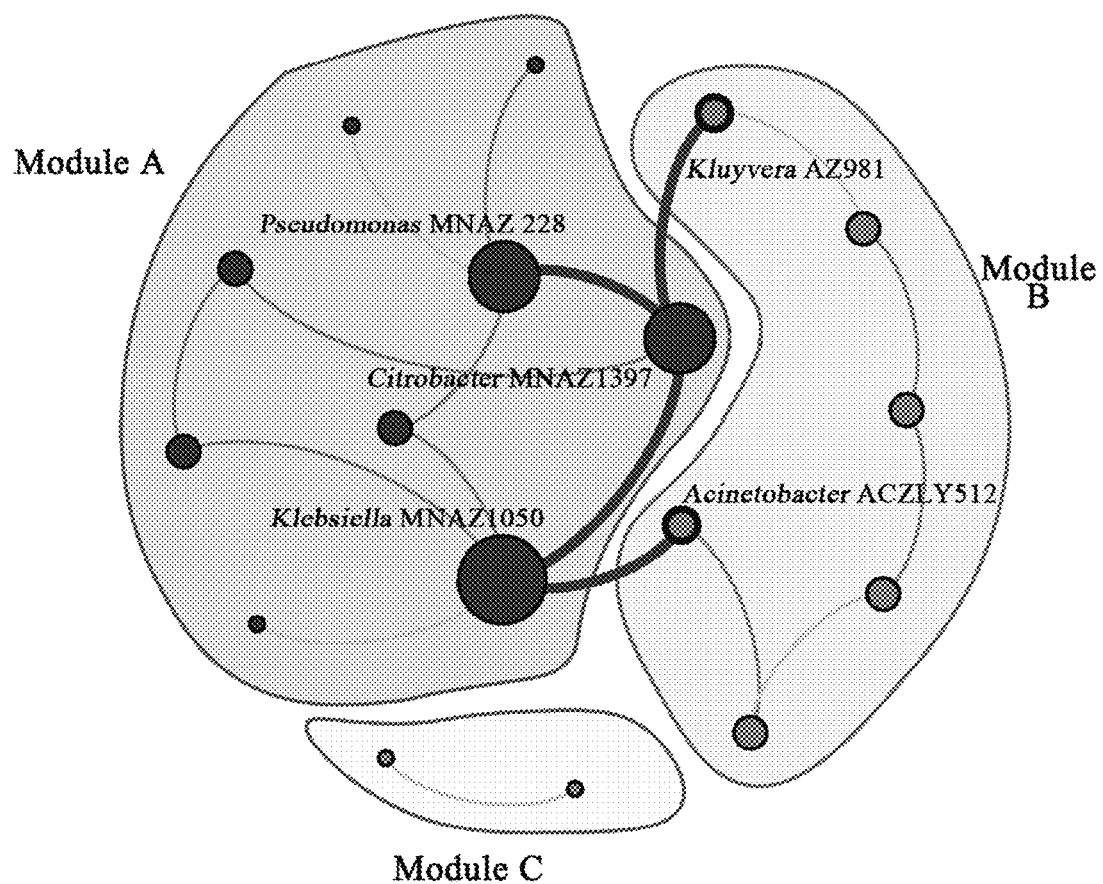
Figure 2:
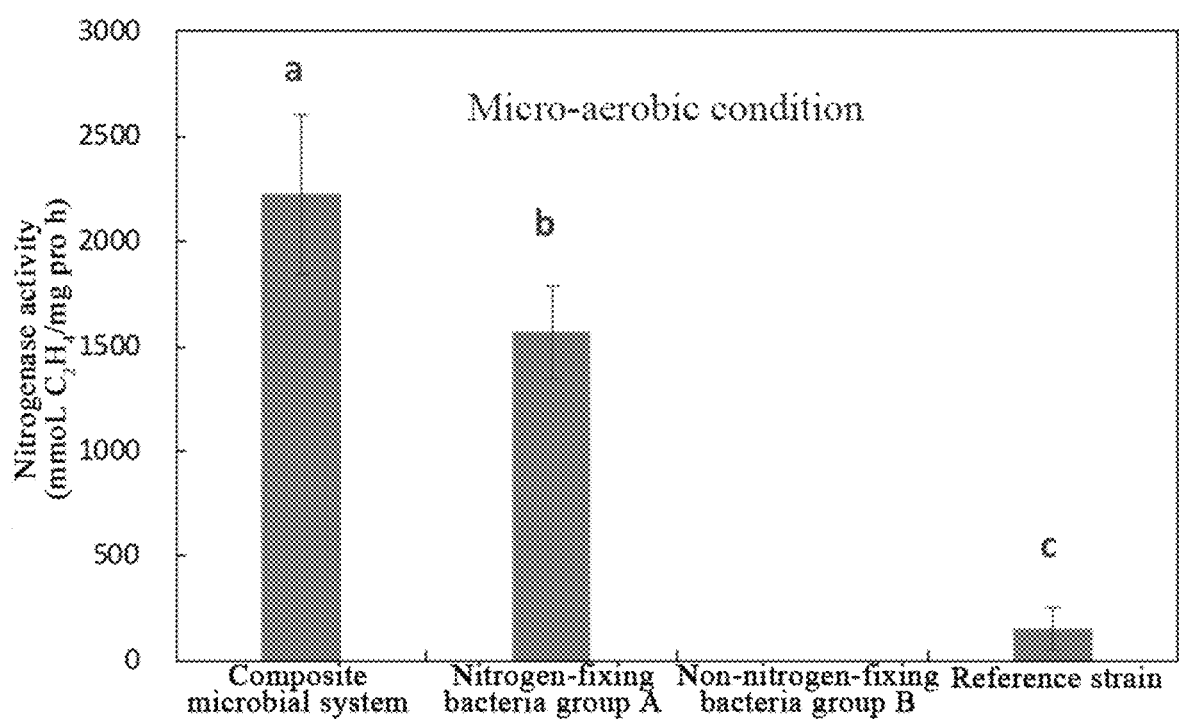
FIG. 2 illustrates nitrogenase activity of an enhanced efficient nitrogen-fixing composite microbial system under micro-aerobic condition, where *Azotobacter chroococcum* ACCC 10006 is used as reference strain, and different letters indicate that there are significant differences between treatments ($p<0.05$).

2. Bioinformatics Analysis and Construction of Composite Microbial System 1) based on results of 16S rDNA sequence analysis, the 969 strains are subjected to taxonomic analysis with results suggesting that the 969 strains are distributed in 44 genera, of which a first five genera, namely *Pantoea, Klebsiella, Acinetobacter, Pseudomonas* and *Kluyvera* (see FIG. 1A-FIG. 1B), covering 80% of the 969 strains;

2) the above 969 bacteria can be classified into 152 species in terms of 16S rDNA, then network analysis is performed by using MENA (http://ieg4.rccc.ou.edu/mena/) with relative abundance of these 152 species as input data, and the strain of highest number in each species as representative strain, and a network is established by Random Matrix Theory (RMT) with a set threshold of 0.9, then the data is visualized by Cytoscape3.6.1;

results: the final microbial network contains 17 representative strains, which are divided into three modules, including module A, module B and module C (see FIG. 1A-FIG. 1B); the three points with the highest degree coefficients in module A are *Klebsiella* MNAZ1050, *Citrobacter* MNAZ1397 and *Pseudomonas* MNAZ228, respectively, all being nitrogen-fixing bacteria and with a relative abundance ratio of 5:2:1; module B is interconnected with module A through *Acinetobacter* ACZLY512 and *Kluyvera* AZ981, both of which are non-nitrogen-fixing bacteria with a relative abundance ratio of 2:1; and module C is an independent module that has no interaction with either module A or module B;

3) in view of the relationship among the above microorganisms, *Klebsiella* MNAZ1050, *Citrobacter* MNAZ1397 and *Pseudomonas* MNAZ228 with the highest degree coefficients in module A are selected as the representative strains, and the three strains form a nitrogen-fixing bacteria group A with a ratio of 5:2:1; then *Acinetobacter* ACZLY512 and *Kluyvera* AZ981 related with module A in the module B are selected as representative strains of non-nitrogen-fixing bacteria and form a non-nitrogen-fixing bacteria group B, where the two strains are in a ratio of 2:1; the nitrogen-fixing bacteria group A and non-nitrogen-fixing bacteria group B form an enhanced efficient nitrogen-fixing composite microbial system, with the above five strains showing positive interaction in network analysis.

3. Verification of Nitrogen Fixation Effect of Composite Microbial System

Acetylene reduction method is used to measure the strains in terms of nitrogenase activity in the composite microbial system, with specific method as follows:

single colonies of strains to be detected are picked out from R2A solid medium and inoculated into a 4 mL R2A liquid medium, then cultured overnight at 28° C. with shaking table at 160 rpm to obtain a bacterial solution, which is centrifuged at 4° C. for 10 min the next day at 5,000 rpm, with supernatant being removed and the remaining bacteria is subjected to resuspension and washing twice with 0.9% normal saline of its same amount, followed by centrifugation for 10 min under the same conditions to remove the residual culture medium, antibiotics and bacterial metabolites; the bacterial solution after washing is adjusted in terms of $OD_{600}$ to 1.0; then 4.5 mL DN nitrogen-free liquid culture medium and 0.5 mL bacterial solution with $OD_{600}$ of 1.0 are added to a 20 mL sterile headspace vial, so that the initial $OD_{600}$ of the culture liquid is 0.1; each sample is set with 5 repetition tests; each headspace vial is replaced with argon gas for 4 min to purge the air in the headspace vial, after the headspace vial is filled with argon gas, 1% oxygen (micro-aerobic condition) or 21% oxygen (normal air oxygen content) and acetylene gas accounting for 10% of the bottle volume are injected into the headspace vial, then the vial is placed at a shaking table for culture at 28° C. and 160 rpm, with time being recorded, and the ethylene content is detected after 12 h by gas chromatography, and nitrogenase activity is also calculated.

Among them, the DN nitrogen-free liquid culture medium includes components of: sucrose 10.0 g, malic acid 5 g, dipotassium hydrogen phosphate monohydrate 0.2 g, potassium dihydrogen phosphate monohydrate 0.4 g, sodium chloride 0.1 g, ferric chloride 0.01 g, sodium molybdate 0.002 g, magnesium sulfate heptahydrate 0.02 g and calcium chloride monohydrate 0.002 g.

The nitrogenase activity of composite microbial system constructed by different strains under micro-aerobic and aerobic conditions is described in detail below.

1) Under the 1% micro-aerobic condition, the *Klebsiella* MNAZ1050, *Citrobacter* MNAZ1397 and *Pseudomonas* MNAZ228 in nitrogen-fixing bacteria group A are mixed according to the ratio of 5:2:1 with reference of above bioinformatics analysis results, while *Acinetobacter* ACZLY512 and *Kluyvera* AZ981 in non-nitrogen-fixing bacteria group B are mixed according to the ratio of 2:1, on this basis, the differences in nitrogenase activities between nitrogen-fixing bacteria group A and non-nitrogen-fixing bacteria group B are verified in different combinations, as shown in Table 1.

TABLE 1 nitrogenase activity of nitrogen-fixing bacteria group A and non-nitrogen-fixing bacteria group B in different proportions under micro-aerobic condition

| Micro-aerobic condition number | Nitrogen-fixing bacteria group A (proportion) | | | Non-fixing bacteria group B (proportion) | | Activity $C_2H_4$/mg pro · hr | Variance |
|---|---|---|---|---|---|---|---|
| | MNAZ1050 5 | MNAZ1397 2 | MNAZ228 1 | ACZLY512 2 | AZ981 1 | | |
| 1 | 1 | | | 0 | | 1,569.8 | 221.7 |
| 2 | 0 | | | 1 | | 0.0 | 0.0 |
| 3 | 1 | | | 1 | | 2,224.1 | 378.2 |
| 4 | 2 | | | 1 | | 2,113.0 | 203.9 |
| 5 | 1 | | | 2 | | 1,801.9 | 189.2 |
| Reference strain ACCC10006 | | | | | | 152.6 | 100.2 |

As can be seen from Table 1, there is no nitrogenase activity when the composite microbial system is constituted only by non-nitrogen-fixing bacteria group B, while various degrees of nitrogenase activities exist when the nitrogen-fixing bacteria group A and nitrogen-fixing bacteria group B are combined according to different combinations, and the nitrogenase activity of nitrogen-fixing bacteria group A combining nitrogen-fixing bacteria group B is the most significant when the ratio of nitrogen-fixing bacteria group A to nitrogen-fixing bacteria group B is 1:1, with nitrogenase activity being as high as 2,224.1 $C_2H_4$/mg protein·hour (pro·hr); compared with nitrogen-fixing bacteria group A, the nitrogenase activity of enhanced efficient nitrogen-fixing composite microbial system is increased by 42%, with significant difference (p<0.05); the nitrogenase activity of the enhanced efficient nitrogen-fixing composite microbial system is 15 times that of the reference strain *Azotobacter chroococcum* ACCC 10006, where the reference strain comes from Agricultural Culture Collection of China.

Under the 1% micro-aerobic condition, the effect of composite microbial system formed by mixing nitrogen-fixing bacteria group A and non-nitrogen-fixing bacteria group B in different combinations yet in a same ratio of 1:1 is verified, see Table 2 for the results:

TABLE 2

Nitrogenase activity of nitrogen-fixing composite microbial system formed by different proportions under micro-aerobic conditions

| Micro-aerobic condition number | Nitrogen-fixing bacteria group A (proportion) 1 | | | Non-nitrogen-fixing bacteria group B (proportion) 1 | | Nitrogenase activity $C_2H_4$/mg pro · hr | Variance |
|---|---|---|---|---|---|---|---|
| | MNAZ1050 | MNAZ1397 | MNAZ228 | ACZLY512 | AZ981 | | |
| 1 | 1 | | | | | 1,261.6 | 160.1 |
| 2 | | 1 | | | | 1,092.5 | 232.9 |
| 3 | | | 1 | | | 971.9 | 79.8 |
| 4 | | | | 1 | | 0.0 | 0.0 |
| 5 | | | | | 1 | 0.0 | 0.0 |
| 6 | 1 | 1 | 1 | | | 1,439.0 | 198.1 |
| 7 | 0 | 2 | 1 | | | 1,083.2 | 120.0 |
| 8 | 1 | 2 | 1 | | | 1,319.8 | 158.8 |
| 9 | 5 | 2 | 1 | | | 1,569.8 | 221.7 |
| 10 | 7 | 2 | 1 | | | 1,509.7 | 120.1 |
| 11 | 5 | 0 | 1 | | | 1,198.7 | 190.2 |
| 12 | 5 | 1 | 1 | | | 1,397.6 | 202.1 |
| 13 | 5 | 4 | 1 | | | 1,391.5 | 120.1 |
| 14 | 5 | 2 | 0 | | | 1,228.7 | 234.9 |
| 15 | 5 | 2 | 2 | | | 1,541.0 | 139.2 |
| 16 | 5 | 2 | 1 | 1 | | 1,992.9 | 269.1 |
| 17 | 5 | 2 | 1 | | 1 | 1,870.3 | 229.7 |
| 18 | 5 | 2 | 1 | 1 | 1 | 2,009.1 | 198.9 |
| 19 | 5 | 2 | 1 | 2 | 1 | 2,224.1 | 378.2 |
| 20 | 5 | 2 | 1 | 1 | 2 | 1,899.2 | 200.8 |
| Reference strain ACCC10006 | | | | | | 152.6 | 100.2 |

It can be seen from Table 2 that any nitrogen-fixing bacteria of *Klebsiella* MNAZ1050, *Citrobacter* MNAZ1397 and *Pseudomonas* MNAZ228 in the nitrogen-fixing bacteria group A, when used alone, have high nitrogenase activity, which is 6-8 times that of the reference strain *Azotobacter chroococcum* ACCC 10006, and when any two nitrogen-fixing bacteria are used in combination as compared to any one strain of nitrogen-fixing bacteria alone, the nitrogenase activity is enhanced, and the highest nitrogenase activity is 1,569.8 $C_2H_4$/mg pro·hr when *Klebsiella* MNAZ1050, *Citrobacter* MNAZ1397 and *Pseudomonas* MNAZ228 are mixed in the ratio of 5:2:1 in nitrogen-fixing bacteria group A.

However, *Acinetobacter* ACZLY512 and *Kluyvera* AZ981 in non-nitrogen-fixing bacteria group B show no nitrogenase activity when either non-nitrogen-fixing bacteria is used alone; when non-nitrogen-fixing bacteria group B and nitrogen-fixing bacteria group A are combined at a ratio of 1:1, with at least one non-nitrogen-fixing strain of non-nitrogen-fixing bacteria group B being selected for use in conjunction with nitrogen-fixing bacteria group A, all exhibit higher nitrogenase activity than that of nitrogen-fixing bacteria group A alone, and the highest nitrogenase activity appears when *Klebsiella* MNAZ1050, *Citrobacter* MNAZ1397 and *Pseudomonas* MNAZ228 in nitrogen-fixing bacteria group A are mixed in the ratio of 5:2:1, and *Acinetobacter* ACZLY512 and *Kluyvera* AZ981 in non-nitrogen-fixing bacteria group B are mixed in the ratio of 2:1, and the nitrogenase activity of 2,224.1 $C_2H_4$/mg prohr, which is consistent with the above bioinformatics analysis results.

2) Under the condition of 21% normal air oxygen content, the differences of nitrogenase activities between nitrogen fixing bacteria group A and non-nitrogen fixing bacteria group B are verified under the premise of mixing *Klebsiella* MNAZ1050, *Citrobacter* MNAZ1397 and *Pseudomonas* MNAZ228 in the ratio of 5:2:1 in nitrogen-fixing bacteria group A and *Acinetobacter* ACZLY512 and *Kluyvera* AZ981 in the ratio of 2:1 in non-nitrogen-fixing bacteria group B according to the results of the above bioinformatics analysis, and the specific combinations are shown in Table 3.

TABLE 3

Nitrogenase activity of nitrogen-fixing bacteria group A and non-nitrogen-fixing bacteria group B in different ratios under aerobic conditions

| Aerobic condition number | Nitrogen-fixing bacteria group A (proportion) | | | Non-nitrogen-fixing bacteria group B (proportion) | | Activity | |
| --- | --- | --- | --- | --- | --- | --- | --- |
| | MNAZ1050 5 | MNAZ1397 2 | MNAZ228 1 | ACZLY512 2 | AZ981 1 | $C_2H_4$/mg pro · hr | Variance |
| 1 | 1 | | | 0 | | 95.2 | 31.3 |
| 2 | 0 | | | 1 | | 0.0 | 0.0 |
| 3 | 1 | | | 1 | | 1048.1 | 246.5 |
| 4 | 2 | | | 1 | | 891.0 | 190.2 |
| 5 | 1 | | | 2 | | 602.0 | 119.0 |
| Reference strain ACCC10006 | | | | | | 17.7 | 7.3 |

Figure 3:
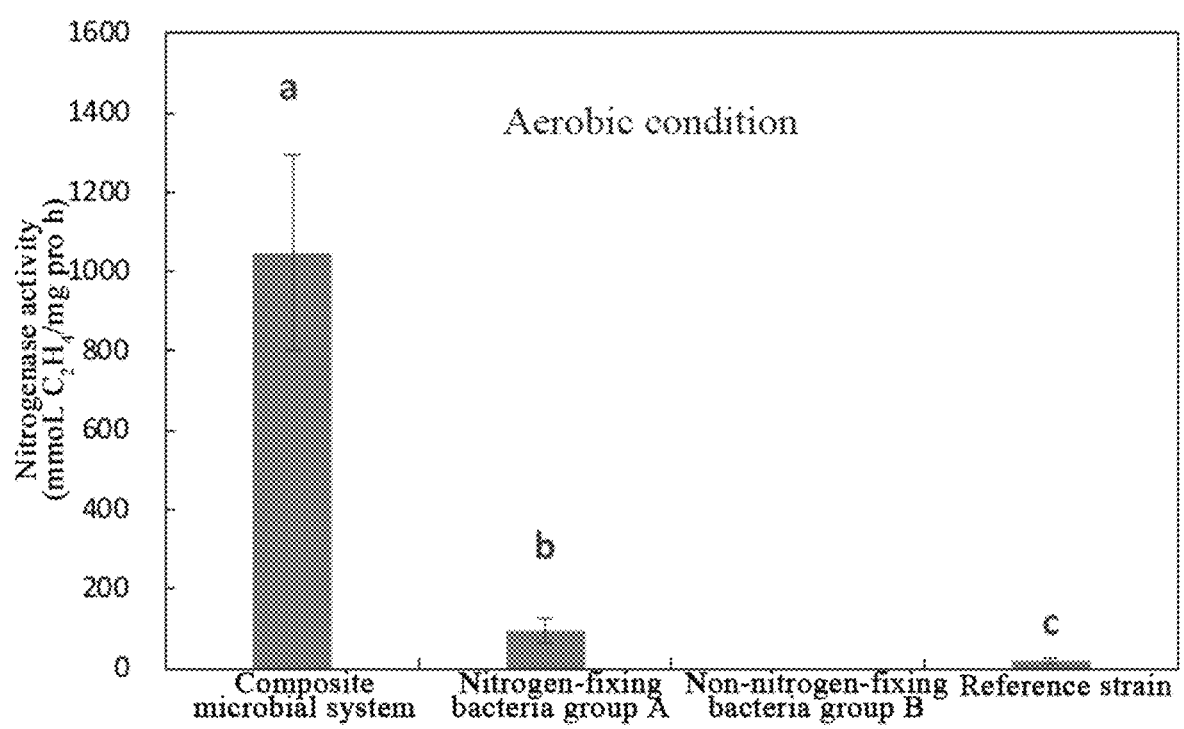
FIG. 3 shows the nitrogenase activity of the nitrogenase activity of an enhanced efficient nitrogen-fixing composite microbial system under aerobic condition, where *Azotobacter chroococcum* ACCC 10006 is used as the reference strain, and different letters indicate that there are significant differences between treatments ($p<0.05$).

As can be seen from Table 3, there is no nitrogenase activity when only non-nitrogen-fixing bacteria group B constitutes the composite microbial system (see FIG. 3), and various nitrogenase activities exist when nitrogen-fixing bacteria group A and nitrogen-fixing bacteria group B are mixed in different combinations, with the most significant nitrogenase activity appears when the ratio of nitrogen-fixing bacteria group A to nitrogen-fixing bacteria group B is 1:1, with nitrogenase activity being as high as 1,048.1 $C_2H_4$/mg prohr; compared with nitrogen-fixing bacteria group A, the nitrogenase activity of the enhanced efficient nitrogen-fixing composite microbial system is increased 10 times with significant difference ($p<0.05$); the nitrogenase activity of the enhanced efficient nitrogen-fixing composite microbial system is 59 times that of the reference strain *Azotobacter chroococcum* ACCC 10006, where the reference strain comes from Agricultural Culture Collection of China.

Under the condition of 21% normal air oxygen content, the effect of composite microbial system constituted by mixing nitrogen-fixing bacteria group A and non-nitrogen-fixing bacteria group B in different combinations yet in a same ratio of 1:1 is verified, with result as shown in Table 4.

TABLE 4

Nitrogenase activity of nitrogen-fixing composite microbial system formed by different combinations under aerobic conditions

| Aerobic condition number | Nitrogen-fixing bacteria group A (proportion) | | | Non-nitrogen fixation group B (proportion) | | Activity $C_2H_4$/mg pro·hr | Variance |
|---|---|---|---|---|---|---|---|
| | MNAZ1050 | MNAZ1397 | MNAZ228 | ACZLY512 | AZ981 | | |
| 1 | 1 | | | | | 22.9 | 0.5 |
| 2 | | 1 | | | | 18.7 | 6.2 |
| 3 | | | 1 | | | 13.6 | 2.2 |
| 4 | | | | 1 | | 0.0 | 0.0 |
| 5 | | | | | 1 | 0.0 | 0.0 |
| 6 | 1 | 1 | 1 | | | 92.8 | 15.9 |
| 7 | 0 | 2 | 1 | | | 23.9 | 15.0 |
| 8 | 1 | 2 | 1 | | | 67.9 | 10.4 |
| 9 | 5 | 2 | 1 | | | 95.2 | 31.3 |
| 10 | 7 | 2 | 1 | | | 88.0 | 21.7 |
| 11 | 5 | 0 | 1 | | | 89.2 | 23.0 |
| 12 | 5 | 1 | 1 | | | 90.9 | 10.2 |
| 13 | 5 | 4 | 1 | | | 81.2 | 21.1 |
| 14 | 5 | 2 | 0 | | | 79.1 | 13.9 |
| 15 | 5 | 2 | 2 | | | 66.9 | 24.0 |
| 16 | 5 | 2 | 1 | 1 | | 692.0 | 182.3 |
| 17 | 5 | 2 | 1 | | 1 | 497.8 | 138.8 |
| 18 | 5 | 2 | 1 | 1 | 1 | 920.3 | 272.4 |
| 19 | 5 | 2 | 1 | 2 | 1 | 1,048.1 | 246.5 |
| 20 | 5 | 2 | 1 | 1 | 2 | 582.2 | 201.9 |
| Reference strain ACCC10006 | | | | | | 17.7 | 7.3 |

It can be seen from Table 4 that any nitrogen-fixing bacteria of *Klebsiella* MNAZ1050, *Citrobacter* MNAZ1397 and *Pseudomonas* MNAZ228 in nitrogen-fixing bacteria group A have nitrogenase activity when used alone, and the nitrogenase activity of any two nitrogen-fixing bacteria in combination is higher than that of any nitrogen-fixing bacteria alone; compared with any combination of two strains of nitrogen-fixing bacteria, the nitrogenase activity of three nitrogen-fixing bacteria is improved when used at the same time, and the highest nitrogenase activity is 95.2 $C_2H_4$/mg prohr when *Klebsiella* MNAZ1050, *Citrobacter* MNAZ1397 and *Pseudomonas* MNAZ228 are mixed in the ratio of 5:2:1 in nitrogen-fixing bacteria group A; on the whole, however, under the condition of 21% normal air oxygen content, the nitrogenase activity of *Klebsiella* MNAZ1050, *Citrobacter* MNAZ1397 and *Pseudomonas* MNAZ228 in nitrogen-fixing bacteria group A is all lower than 100 $C_2H_4$/mg prohr (Table 3), far lower than that under micro-aerobic condition (all higher than 900 $C_2H_4$/mg pro·hr, see Table 2), indicating that oxygen exerts an inhibitory effect on nitrogen fixation.

However, *Acinetobacter* ACZLY512 and *Kluyvera* AZ981 in non-nitrogen-fixing bacteria group B shows no nitrogenase activity when either non-nitrogen-fixing bacteria is used alone. When non-nitrogen-fixing bacteria group B and nitrogen-fixing bacteria group A are combined at a ratio of 1:1, with at least one non-nitrogen-fixing bacteria strain in non-nitrogen-fixing bacteria group B is used in combination with nitrogen-fixing bacteria group A, the activity of nitrogenase is greatly increased compared with that when nitrogen-fixing bacteria group A is used alone; moreover, when *Klebsiella* MNAZ1050, *Citrobacter* MNAZ1397 and *Pseudomonas* MNAZ228 in nitrogen-fixing bacteria group A are mixed at a ratio of 5:2:1, and *Acinetobacter* ACZLY512 and *Kluyvera* AZ981 in non-nitrogen-fixing bacteria group B are mixed in a ratio of 2:1, with a highest nitrogenase activity of 1,048.1 $C_2H_4$/mg pro·hr, which is consistent with the results of above bioinformatics analysis.

Figure 4:
FIG. 4 shows growth of maize applied with the enhanced efficient nitrogen-fixing composite microbial system.

Embodiment 2 Application of Enhanced Efficient Nitrogen-Fixing Composite Microbial System in Promoting Maize Growth 1) maize seeds of Zhengdan No. 958 are firstly sterilized with 75% alcohol for 3 minutes (min), then sterilized with 5% sodium hypochlorite for 8 min, and washed with sterile water for three times; then the washed maize seeds are buried to a depth of 1 centimeter (cm) in sterile quartz sand, followed by watering thoroughly with sterile water and accelerated germination in an incubator in the dark at 30° C. for 3 days; after that, then the germinated maize seeds are transferred to an artificial climate box, with illumination for 16 h in the daytime and 8 h in the dark, and air moisture of 60%;

2) after the maize seeds grow into maize seedlings with three leaves, they are carefully pulled out of the quartz sand and the endosperms are removed; then the enhanced efficient nitrogen-fixing composite microbial system is prepared by mixing nitrogen-fixing bacteria group A and non-nitrogen-fixing bacteria group B in a ratio of 1:1; the maize seedlings are soaked with roots in the composite microbial system for 10 min, while maize roots in the control group are soaked in sterile water for 10 min; after soaking, the maize seedlings are planted in sterile quartz sand, with each culture basin is planted with two maize seedlings of same growth situation;

the enhanced efficient nitrogen-fixing composite microbial system is prepared as follows: inoculating *Klebsiella* MNAZ1050, *Citrobacter* MNAZ1397, *Pseudomonas* MNAZ228, *Acinetobacter* ACZLY512 and *Kluyvera* AZ981 respectively into 30 mL R2A liquid medium, subjecting to culture overnight at 28° C. in a shaking table at 160 rpm to obtain a bacterial solution the next day, centrifuging at 4° C. for 10 min at 5,000 rpm, discarding the supernatant, resuspending and washing the remaining bacteria twice with the same amount of 0.9% normal saline, and centrifuging for 10 min under the same conditions to remove the residual culture medium, antibiotics and bacterial metabolites;

adjusting the $OD_{600}$ of the washed bacteria to 1.0, then mixing with *Klebsiella* MNAZ1050, 8 mL of *Citrobacter* MNAZ1397 and 4 mL of *Pseudomonas* MNAZ228 to prepare a bacterial solution of nitrogen-fixing bacteria group A with the ratio of 5:2:1; and 20 mL of *Acinetobacter* ACZLY512 and 10 mL of *Kluyvera* AZ981 are mixed to prepare a bacterial solution of non-nitrogen-fixing bacteria group B with the ratio of 2:1; finally, 30 mL bacterial solution of nitrogen-fixing bacteria group A and 30 mL bacterial solution of non-nitrogen-fixing bacteria group B are mixed to prepare the enhanced efficient nitrogen-fixing composite microbial system;

3) after maize planting, the maize seedlings are watered with 500 mL sterile water every day, and applied with 500 mL nutrient solution with 50% reduction of nitrogen every three days;

the mother liquid of nutrient solution with 50% reduction of nitrogen includes potassium nitrate 303.3 grams per liters (g/L), calcium nitrate tetrahydrate 472.32 g/L, ammonium dihydrogen phosphate 115.08 g/L, magnesium sulfate heptahydrate 246.48 g/L, sodium ferric ethylene diamine tetraacetic acid 9.8 g/L, trace element liquid (including boric acid 1.546 g/L, manganese sulfate monohydrate 0.338 g/L, zinc sulfate heptahydrate 0.576 g/L, copper sulfate pentahydrate 0.124 g/L, molybdic acid 0.080 g/L), 1 mL of each mother liquor is diluted to 1 L when being used;

4) on the 30th day of maize growth, 60 mL of the enhanced efficient nitrogen-fixing composite microbial system bacteria solution is diluted to 500 mL with sterile water and then poured into the roots of maize seedlings, while that of the control group are applied with the same volume of sterile water; and 5) under the condition of 50% reduction of nitrogen fertilizer application, after 65 days of maize growth, the root biomass of maize applied with enhanced efficient nitrogen-fixing composite microbial system is 14.75 g (dry weight), which is increased by 23% compared with that of the control group, and the aboveground biomass of maize is 29.44 g (dry weight), which is increased by 32% compared with that of the control group. The whole maize biomass is increased by 29% (see FIG. 4).

The above results show that the enhanced efficient nitrogen-fixing composite microbial system of the present disclosure can not only supplement nitrogen nutrition for maize through biological nitrogen fixation, but also have root promotion effect by increasing the biomass of maize root system.

The above-mentioned embodiments only describe the preferred mode of the present disclosure, but do not limit the scope of the present disclosure. On the premise of not departing from the design spirit of the present disclosure, all kinds of modifications and improvements made by ordinary technicians in the field to the technical scheme of the present disclosure shall fall within the scope of protection determined by the claims of the present disclosure.

What is claimed is:

1. A nitrogen-fixing composite microbial system, comprising nitrogen-fixing bacteria and non-nitrogen-fixing bacteria, wherein the nitrogen-fixing bacteria comprise *Klebsiella* MNAZ1050 (*Klebsiella* sp.), *Citrobacter* MNAZ1397 (*Citrobacter* sp.), and *Pseudomonas* MNAZ228 (*Pseudomonas* sp.), and the non-nitrogen-fixing bacteria comprise *Acinetobacter* ACZLY512 (*Acinetobacter* sp.) and *Kluyvera* AZ981 (*Kluyvera* sp.);

wherein the *Klebsiella* MNAZ1050, *Citrobacter* MNAZ1397, and the *Pseudomonas* MNAZ228 are preserved in China General Microbiological Culture Collection Center under a same preservation date of May 6, 2021, with a preservation number of *Klebsiella* MNAZ1050 being CGMCC No. 22270, and preservation numbers of *Citrobacter* MNAZ1397 and *Pseudomonas* MNAZ228 being CGMCC No. 22267 and CGMCC No. 22266 respectively; and the *Acinetobacter* ACZLY512 and the *Kluyvera* AZ981 are preserved in China General Microbiological Culture Collection Center under the preservation date of May 6, 2021, with a preservation number of *Acinetobacter* ACZLY512 being CGMCC No. 22268 and a preservation number of *Kluyvera* AZ981 being CGMCC No. 22269.

2. A microbial inoculum, comprising the nitrogen-fixing composite microbial system according to claim 1 as active ingredients, wherein the nitrogen-fixing composite microbial system comprises nitrogen-fixing bacteria and non-nitrogen-fixing bacteria in a ratio of (1-2):(1-2).

3. The microbial inoculum according to claim 2, wherein the nitrogen-fixing bacteria comprises *Klebsiella* MNAZ1050, *Citrobacter* MNAZ1397, and *Pseudomonas* MNAZ228 in a ratio of (1-7):(1-4):(1-2); and the non-nitrogen-fixing bacteria comprises *Acinetobacter* ACZLY512 and *Kluyvera* AZ981 mixed in a ratio of (1-2):(1-2).

4. An application of the nitrogen-fixing composite microbial system in preparing any one of following microbial inoculums:

(1) microbial inoculum for improving nitrogen fixation performance of food crops and agronomic crops;

(2) microbial inoculum for increasing aboveground biomass of food crops and agronomic crops; and (3) microbial inoculum for increasing root biomass of food crops and agronomic crops;

wherein the nitrogen-fixing composite microbial system comprises nitrogen-fixing bacteria and non-nitrogen-fixing bacteria;

wherein the nitrogen-fixing bacteria comprise *Klebsiella* MNAZ1050 (*Klebsiella* sp.), *Citrobacter* MNAZ1397 (*Citrobacter* sp.), and *Pseudomonas* MNAZ228 (*Pseudomonas* sp.), and the non-nitrogen-fixing bacteria comprise *Acinetobacter* ACZLY512 (*Acinetobacter* sp.) and *Kluyvera* AZ981 (*Kluyvera* sp.);

wherein the *Klebsiella* MNAZ1050, *Citrobacter* MNAZ1397, and the *Pseudomonas* MNAZ228 are preserved in China General Microbiological Culture Collection Center under a same preservation date of May 6, 2021, with a preservation number of *Klebsiella* MNAZ1050 being CGMCC No. 22270, and preservation numbers of *Citrobacter* MNAZ1397 and *Pseudomonas* MNAZ228 being CGMCC No. 22267 and CGMCC No. 22266 respectively; and wherein the *Acinetobacter* ACZLY512 and the *Kluyvera* AZ981 are preserved in China General Microbiological Culture Collection Center under the preservation date of May 6, 2021, with a preservation number of *Acinetobacter* ACZLY512 being CGMCC No. 22268 and a preservation number of *Kluyvera* AZ981 being CGMCC No. 22269.

\* \* \* \* \*